US011472765B2

(12) United States Patent
Iida et al.

(10) Patent No.: US 11,472,765 B2
(45) Date of Patent: Oct. 18, 2022

(54) PRODUCTION METHOD FOR 1,4-CYCLOHEXANEDICARBOXYLIC ACID DERIVATIVE, 1,4-DICYANOCYCLOHEXANE AND 1,4-BIS(AMINOMETHYL)CYCLOHEXANE

(71) Applicant: Mitsubishi Gas Chemical Company, Inc., Chiyoda-ku (JP)

(72) Inventors: Akifumi Iida, Niigata (JP); Aoi Yamazoe, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 29 days.

(21) Appl. No.: 16/968,011

(22) PCT Filed: Apr. 11, 2019

(86) PCT No.: PCT/JP2019/015726
§ 371 (c)(1),
(2) Date: Aug. 6, 2020

(87) PCT Pub. No.: WO2019/198779
PCT Pub. Date: Oct. 17, 2019

(65) Prior Publication Data
US 2021/0032191 A1  Feb. 4, 2021

(30) Foreign Application Priority Data

Apr. 11, 2018 (JP) .............. JP2018-076270

(51) Int. Cl.
*C07C 209/48* (2006.01)
*C07C 51/43* (2006.01)
*C07C 253/22* (2006.01)
*C07C 211/18* (2006.01)
*C07C 255/46* (2006.01)

(52) U.S. Cl.
CPC .......... *C07C 209/48* (2013.01); *C07C 51/43* (2013.01); *C07C 253/22* (2013.01); *C07C 211/18* (2013.01); *C07C 255/46* (2013.01)

(58) Field of Classification Search
None
See application file for complete search history.

(56) References Cited

U.S. PATENT DOCUMENTS

| | | | |
|---|---|---|---|
| 5,202,475 A | 4/1993 | Cook et al. | |
| 2010/0216905 A1 | 8/2010 | Kuwamura et al. | |
| 2013/0197270 A1 | 8/2013 | Yoshimura et al. | |

FOREIGN PATENT DOCUMENTS

| | | |
|---|---|---|
| CN | 101591237 A | 12/2009 |
| CN | 105016944 A | 11/2015 |
| EP | 2 626 344 A1 | 8/2013 |
| GB | 1087161 A | 10/1967 |
| JP | 50-10581 | 4/1975 |
| JP | 7-507041 A | 8/1995 |
| JP | 2002-69032 A | 3/2002 |
| JP | 2011-6382 A | 1/2011 |
| JP | 5448987 B2 | 3/2014 |
| WO | 8-157419 A | 6/1996 |
| WO | WO 2009/051114 A1 | 4/2009 |
| WO | WO 2012/046782 A1 | 4/2012 |
| WO | WO 2014/080980 A1 | 5/2014 |

OTHER PUBLICATIONS

English translation of Qui et al. (CN 101591237, pub date Dec. 2, 2009) (Year: 2009).*
International Search Report dated Jun. 25, 2019 in PCT/JP2019/015726 filed on Apr. 11, 2019, 2 pages.

* cited by examiner

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

A production method for producing a 1,4-cyclohexanedicarboxylic acid derivative, involves subjecting an aqueous ammonia solution of 1,4-cyclohexanedicarboxylic acid to heat concentration, thereby precipitating a 1,4-cyclohexanedicarboxylic acid derivative as a crystal.

17 Claims, No Drawings

PRODUCTION METHOD FOR 1,4-CYCLOHEXANEDICARBOXYLIC ACID DERIVATIVE, 1,4-DICYANOCYCLOHEXANE AND 1,4-BIS(AMINOMETHYL)CYCLOHEXANE

TECHNICAL FIELD

The present invention relates to a production method for a 1,4-cyclohexanedicarboxylic acid derivative, 1,4-dicyanocyclohexane and 1,4-bis(aminomethyl)cyclohexane.

BACKGROUND ART 1,4-Bis(aminomethyl)cyclohexane is an industrially important compound, which is used as a raw material for an epoxy curing agent, polyamide, polyurethane, etc. 1,4-Bis (aminomethyl)cyclohexane has two isomers: cis isomer and trans isomer, resulting from the cyclohexane ring. For polymers for which 1,4-bis(aminomethyl)cyclohexane is used, it is known that the physical properties are significantly changed depending on the isomeric ratio between cis isomer and trans isomer.

For example, for polyurethane for which 1,4-bisisocyanatomethylcyclohexane derived from 1,4-bis(aminomethyl) cyclohexane is used, it is known that the higher the content rate of trans isomer is, the more the requisite physical properties depending on various applications are improved (Patent Literature 1).

As the method for producing 1,4-bis(aminomethyl)cyclohexane, mention may be made of several methods, but a method is known in which 1,4-cyclohexanedicarboxylic acid is subjected to amidation and dehydration reactions to produce 1,4-dicyanocyclohexane, and 1,4-dicyanocyclohexane is subjected to a nitrile hydrogenation reaction to produce 1,4-bis(aminomethyl)cyclohexane. Upon producing 1,4-dicyanocyclohexane from 1,4-cyclohexanedicarboxylic acid, a crystal of 1,4-cyclohexanedicarboxylic acid or derivative thereof is often used as a raw material.

As the method for producing a crystal of 1,4-cyclohexanedicarboxylic acid or derivative thereof, which is to be a raw material for 1,4-dicyanocyclohexane, the following methods are known. Patent Literature 2 and Patent Literature 3 disclose a method in which an alkali metal salt of terephthalic acid is subjected to nucleus hydrogenation, the catalyst is separated from the obtained reaction solution, and an acid is then added thereto, thereby collecting 1,4-cyclohexanedicarboxylic acid as a crystal. Patent Literature 4 discloses a method in which nucleus hydrogenation is performed on terephthalic acid, the catalyst is separated through thermal filtration, and 1,4-cyclohexanedicarboxylic acid is then collected after purification. Patent Literature 5 discloses a method in which nucleus hydrogenation is performed on terephthalic acid, which is made into an alkali metal salt after the nucleus hydrogenation and then separated from the catalyst, and an acid is added thereto, thereby collecting 1,4-cyclohexanedicarboxylic acid.

CITATION LIST

Patent Literature

Patent Literature 1: International Publication No. WO 2009/051114
Patent Literature 2: Japanese Patent Publication No. 50-10581
Patent Literature 3: Japanese Translation of PCT International Application Publication No. 1995-507041
Patent Literature 4: Japanese Patent Application Laid-Open No. 2002-69032
Patent Literature 5: Japanese Patent No. 5448987

SUMMARY OF INVENTION

Technical Problem

However, in the method described in Patent Literature 2 and Patent Literature 3, a salt is byproduced when the alkali metal salt of 1,4-cyclohexanedicarboxylic acid is neutralized to collect 1,4-cyclohexanedicarboxylic acid as a crystal. Therefore, a step of treating the waste liquid containing the byproduced salt, a step of rinsing the crystal with water to remove the salt from the crystal and the like are required. In the method described in Patent Literature 4, 1,4-cyclohexanedicarboxylic acid and the catalyst are separated through thermal filtration. In such a method, the purity of the obtained 1,4-cyclohexanedicarboxylic acid is low, and therefore, a purification step for increasing the purity of 1,4-cyclohexanedicarboxylic acid is required. In the method described in Patent Literature 5, upon separating 1,4-cyclohexanedicarboxylic acid from the catalyst, it is once made into an alkali metal salt, and then, upon collecting 1,4-cyclohexanedicarboxylic acid as a crystal, it is neutralized. Specifically, a method described in Examples of this literature produces 85% by mass of NaCl based on 100% by mass of 1,4-cyclohexanedicarboxylic acid. Therefore, this method also requires a step of treating the waste liquid containing the byproduced salt, a step of rinsing the crystal with water to remove the salt from the crystal and the like, as in the method described in Patent Literature 3.

The present invention has been made in view of the problems described above, and an object of the present invention is to provide a novel production method for a 1,4-cyclohexanedicarboxylic acid derivative, the method suppressing production of a salt upon collecting a 1,4-cyclohexanedicarboxylic acid derivative as a crystal. Furthermore, the present invention has an object to provide a production method for 1,4-dicyanocyclohexane obtained via the above production method, and a production method for 1,4-bis(aminomethyl)cyclohexane.

Solution to Problem

The present inventors have made diligent researches in order to achieve the objects described above, and consequently have found that the objects described above can be achieved by subjecting an aqueous ammonia solution of 1,4-cyclohexanedicarboxylic acid to heat concentration, leading to completion of the present invention.

Namely, the present invention is as follows:

(1)
A production method for a 1,4-cyclohexanedicarboxylic acid derivative, having a step of subjecting an aqueous ammonia solution of 1,4-cyclohexanedicarboxylic acid to heat concentration, thereby precipitating a 1,4-cyclohexanedicarboxylic acid derivative as a crystal.

(2)
The production method according to (1), wherein the 1,4-cyclohexanedicarboxylic acid derivative is an ammonium salt of 1,4-cyclohexanedicarboxylic acid and/or 4-carboxamidocyclohexane-1-carboxylic acid.

(3)

The production method according to (2), wherein a content of ammonia in the ammonium salt of 1,4-cyclohexanedicarboxylic acid is 0.01 to 2.00 in a molar ratio based on a content of 1,4-cyclohexanedicarboxylic acid in the ammonium salt of 1,4-cyclohexanedicarboxylic acid.
(4)
The production method according to any of (1) to (3), wherein, in the step, a temperature upon the heat concentration is 30 to 200° C.
(5)
The production method according to any of (1) to (4), wherein, in the step, a pressure upon the heat concentration is 0.003 to 2 MPa.
(6)
The production method according to any of (1) to (5), wherein a content of trans isomer of the 1,4-cyclohexanedicarboxylic acid derivative is 70.0 to 99.9% by mass.
(7)
The production method according to any of (1) to (6), wherein the aqueous ammonia solution of 1,4-cyclohexanedicarboxylic acid is obtained by subjecting an aqueous ammonia solution of terephthalic acid to nucleus hydrogenation.
(8)
A production method for 1,4-dicyanocyclohexane, having a step of obtaining 1,4-dicyanocyclohexane by bringing a 1,4-cyclohexanedicarboxylic acid derivative obtained via the production method according to any of (1) to (7) into contact with ammonia for a cyanation reaction.
(9)
A production method for 1,4-bis(aminomethyl)cyclohexane, having a step of obtaining 1,4-bis(aminomethyl) cyclohexane by bringing 1,4-dicyanocyclohexane obtained via the method according to (8) into contact with hydrogen for a hydrogenation reaction.

Advantageous Effects of Invention

The present invention can provide a novel production method for a 1,4-cyclohexanedicarboxylic acid derivative, the method suppressing production of a salt upon collecting a 1,4-cyclohexanedicarboxylic acid derivative as a crystal. Furthermore, the present invention can provide a production method for 1,4-dicyanocyclohexane obtained via the above production method, and a production method for 1,4-bis (aminomethyl)cyclohexane.

DESCRIPTION OF EMBODIMENTS

Hereinafter, an embodiment for performing the present invention (hereinafter, simply referred to as a "present embodiment") will be described in detail, but the present invention is not limited to the present embodiment described below. It is possible to make various modifications to the present invention within a range of not departing from its spirit.

A production method for a 1,4-cyclohexanedicarboxylic acid derivative of the present embodiment (hereinafter, also referred to as a "1,4-CHDA production method") has a step (hereinafter, also referred to as a "heat concentration and precipitation step") of subjecting an aqueous ammonia solution of 1,4-cyclohexanedicarboxylic acid to heat concentration, thereby precipitating a 1,4-cyclohexanedicarboxylic acid derivative as a crystal. In order to collect 1,4-cyclohexanedicarboxylic acid, which is to be used as a raw material for 1,4-dicyanocyclohexane, as a crystal, normally, methods in which an alkali metal salt of 1,4-cyclohexanedicarboxylic acid is neutralized with an acid, as in the methods described in Patent Literatures 2, 3 and 5, are often used. However, these methods require a step of treating the waste liquid containing the byproduced salt, a step of rinsing the crystal with water to remove the salt from the crystal and the like. In contrast, a production method of the present embodiment subjects an aqueous ammonia solution of 1,4-cyclohexanedicarboxylic acid to heat concentration, thereby precipitating a 1,4-cyclohexanedicarboxylic acid derivative, which is to be used as a raw material for 1,4-dicyanocyclohexane, as a crystal. By doing this, production of a salt upon collecting 1,4-cyclohexanedicarboxylic acid as a crystal, as in the methods described in Patent Literatures 2, 3 and 5, can be suppressed. Furthermore, a step of treating the waste liquid containing the salt and the like are not necessary, for example, which is excellent in the production efficiency. On the other hand, in order to collect 1,4-cyclohexanedicarboxylic acid, which is to be used as a raw material for 1,4-dicyanocyclohexane, as a crystal, nucleus hydrogenation may be performed on terephthalic acid and the catalyst may be separated through thermal filtration, as described in Patent Literature 4. However, in such a method, the purity of 1,4-cyclohexanedicarboxylic acid is low, and therefore, a purification step for increasing the purity of 1,4-cyclohexanedicarboxylic acid is required. In contrast, a production method of the present embodiment subjects an aqueous ammonia solution of 1,4-cyclohexanedicarboxylic acid to heat concentration, and can thus precipitate a 1,4-cyclohexanedicarboxylic acid derivative, which is to be used as a raw material for 1,4-dicyanocyclohexane, as a crystal at a high purity. Therefore, the production method of the present embodiment does not need a purification step for increasing the purity of a 1,4-cyclohexanedicarboxylic acid derivative, which is thus excellent in the production efficiency.

In the heat concentration and precipitation step, by heating the aqueous ammonia solution of a 1,4-cyclohexanedicarboxylic acid derivative, at least a part of water is removed. In addition, in the heat concentration and precipitation step, it is preferable that the concentration of ammonia in the aqueous ammonia solution before the heat concentration should be 0.1 to 10% by mass based on the entire amount of the aqueous ammonia solution.

In the heat concentration and precipitation step, it is preferable that the temperature upon the heat concentration (heating temperature) should be 30 to 200° C. When the heating temperature is within the above range, water can be effectively removed from the aqueous ammonia solution by volatilization, producing a 1,4-cyclohexanedicarboxylic acid derivative as a crystal, and as a result, the yield of 1,4-dicyanocyclohexane becomes even higher in the cyanation step, which will be mentioned later. From the same point of view, the heating temperature is more preferably 50 to 200° C. and still more preferably 100 to 200° C. On the other hand, from the viewpoint of increasing the content of trans isomer of the 1,4-cyclohexanedicarboxylic acid derivative as a crystal, the heating temperature is preferably 120 to 200° C. and more preferably 140 to 200° C.

In the present embodiment, the 1,4-cyclohexanedicarboxylic acid derivative produced in the heat concentration and precipitation step may or may not contain 1,4-cyclohexanedicarboxylic acid in a part thereof.

In the heat concentration and precipitation step, it is preferable that the pressure upon the heat concentration should be 0.003 to 2 MPa. When the pressure upon the heat concentration is within the above range, water can be effectively removed from the aqueous ammonia solution by volatilization, producing a 1,4-cyclohexanedicarboxylic acid derivative as a crystal, and the yield of 1,4-dicyanocyclohexane becomes even higher in the cyanation step, which will be mentioned later. In addition, the pressure conditions may be normal pressure conditions, or may be reduced pressure conditions or pressurized conditions. However, from the viewpoint of increasing the content of trans isomer of the 1,4-cyclohexanedicarboxylic acid derivative as a crystal, the pressurized conditions are preferable.

In the heat concentration and precipitation step, the method of heat concentration is not particularly limited as long as water can be removed from the aqueous ammonia solution of 1,4-cyclohexanedicarboxylic acid by volatilization. For the method of heat concentration, from the viewpoint of positively removing water from the aqueous ammonia solution of 1,4-cyclohexanedicarboxylic acid by volatilization to the outside of the system, a method utilizing an open system is preferable.

In the heat concentration and precipitation step, as the method of collecting the 1,4-cyclohexanedicarboxylic acid derivative as a crystal from the heated concentrate, mention may be made of, for example, a method of collecting a crystal by filtering the heated concentrate.

The liquid content of the mother liquor in the 1,4-cyclohexanedicarboxylic acid derivative after the filtration is preferably 5 to 35% by weight, and more preferably 10 to 25% by weight from the viewpoint of operability. The 1,4-cyclohexanedicarboxylic acid derivative after the filtration may be subjected to a subsequent step in a state of containing the mother liquor, or after once removing the crystal, may be dried and then subjected to a subsequent step.

The concentration of the 1,4-cyclohexanedicarboxylic acid derivative after the filtration in the mother liquor is preferably 50 to 100 mol %, and more preferably 70 to 100 mol % based on 100 mol % of ammonia.

In the production method of the present embodiment, the number of times of the heat concentration and precipitation step may be once, or may be multiple times. In the production method of the present embodiment, the aqueous ammonia solution after collecting the crystal through the first heat concentration and precipitation step may be repeatedly used in the second and subsequent heat concentration and precipitation steps to further collect the crystal. In the production method of the present embodiment, the number of times of the heat concentration and precipitation step is multiple times and the 1,4-cyclohexanedicarboxylic acid derivative can thus be thoroughly collected, and therefore, the yield of the 1,4-cyclohexanedicarboxylic acid derivative tends to become even more excellent.

Examples of the 1,4-cyclohexanedicarboxylic acid derivative include one or more selected from the group consisting of an ammonium salt of 1,4-cyclohexanedicarboxylic acid and 4-carboxamidocyclohexane-1-carboxylic acid, and the ammonium salt of 1,4-cyclohexanedicarboxylic acid is preferable from the viewpoint of further increasing the yield of 1,4-dicyanocyclohexane in the cyanation step, which will be mentioned later. On the other hand, as the 1,4-cyclohexanedicarboxylic acid derivative, mention may also be made of 1,4-cyclohexanedicarboxamide, but 1,4-cyclohexanedicarboxamide has a high melting point and is difficult to be dissolved during the reaction, thereby leading to a decrease in reactivity. As a result, byproducts having high boiling point are likely to be formed and the yield tends to be deteriorated. Therefore, the content of 1,4-cyclohexanedicarboxamide in the 1,4-cyclohexanedicarboxylic acid derivative is preferably 10% by mass or less, more preferably 5% by mass or less, and still more preferably 1% by mass or less. On the other hand, the total content of 1,4-cyclohexanedicarboxylic acid, an ammonium salt of 1,4-cyclohexanedicarboxylic acid and 4-carboxamidocyclohexane-1-carboxylic acid in the 1,4-cyclohexanedicarboxylic acid derivative is preferably 90% by mass or more, more preferably 95% by mass or more, and still more preferably 99% by mass or more from the viewpoint of yield and reactivity.

From the viewpoint of further increasing the yield of 1,4-dicyanocyclohexane in the cyanation step, which will be described below, the content of ammonia in the ammonia salt of 1,4-cyclohexanedicarboxylic acid is, based on the content of 1,4-cyclohexanedicarboxylic acid in the ammonium salt of 1,4-cyclohexanedicarboxylic acid, preferably 0.01 to 2.00, more preferably 1.90 or less (for example, 0.10 to 1.90), and still more preferably 1.85 or less (for example, 0.10 to 1.85) in a molar ratio (former/latter).

The content of trans isomer of the 1,4-cyclohexanedicarboxylic acid derivative is preferably 70.0 to 99.9% by mass, more preferably 75.0 to 99.0% by mass, still more preferably 78.0 to 98.0% by mass, and particularly preferably 80.0 to 96.0% by mass.

It is preferable that the aqueous ammonia solution of 1,4-cyclohexanedicarboxylic acid, which is to be used as a raw material in the heat concentration and precipitation step, should be obtained by subjecting an aqueous ammonia solution of terephthalic acid to nucleus hydrogenation. It is preferable that the 1,4-CHDA production method of the present embodiment should have a step (hereinafter, also simply referred to as a "nucleus hydrogenation step") of obtaining 1,4-cyclohexanedicarboxylic acid by subjecting terephthalic acid in an aqueous ammonia solution to a hydrogenation reaction (hereinafter, also simply referred to as a "nucleus hydrogenation reaction"). When the 1,4-CHDA production method has the nucleus hydrogenation step, at least a part of the aqueous ammonia solution included in the reaction solution that has undergone that step can be used as the aqueous ammonia solution in the heat concentration and precipitation step. Therefore, effective utilization of ammonia is enabled.

Nucleus Hydrogenation Step

For the nucleus hydrogenation step, any reaction scheme may be adopted among a slurry bed (batch system and semi-batch system) and a fixed bed (continuous system). In a slurry bed, for example, a catalyst and water are placed in a reactor at first; hydrogen gas is then introduced into the reactor until reaching a predetermined pressure; the suspension is heated and stirred while maintaining the pressure; and the catalyst is reduced to be activated. For the catalyst, for example, a catalyst used for an ordinary nucleus hydrogenation reaction can be employed, and more particularly, one or two or more metal catalysts, preferably precious metal catalysts, such as Ru, Pd, Pt and Rh, can be used. The catalyst may be those in which the metal catalyst described above as an active component is supported on one or two or more supports that are ordinarily used, such as carbon, $Al_2O_3$, $SiO_2$, $SiO_2$—$Al_2O_3$, $TiO_2$ and $ZrO_2$. When a support is used, it is preferable that the amount of the metal catalyst to be supported, which is an active component, should be 0.1 to 10% by mass based on 100% by mass of the support.

In addition, the pressure in the system upon the activation of the catalyst may be an ordinary pressure (the gas phase part is purged with hydrogen) or may be compressed. When compressed, the pressure in the system is preferably 0.1 to 8 MPa, and hydrogen gas may be appropriately introduced into the reactor in order to maintain such a pressure. Furthermore, it is preferable that the activation temperature should be 50 to 250° C. By making conditions upon the activation of the catalyst within the ranges described above, the catalyst can be activated further more effectively and reliably. In addition, the stirring time may be any length as long as it is sufficient for activating the catalyst.

Next, the reactor is cooled and the hydrogen gas remaining in the system is discharged to the outside of the system; terephthalic acid and an aqueous ammonia solution are then placed in the reactor; and furthermore, hydrogen gas is introduced until reaching a predetermined pressure. Upon this, it is preferable that the amount of the terephthalic acid to be placed should be 2 to 20% by mass based on the entire reaction solution. In addition, it is preferable that the amount of the aqueous ammonia solution to be placed should be an amount that provides 200 to 400 mol % of ammonia based on 100 mol % of terephthalic acid. There is no limitation on the amount of the catalyst to be used, and it may be appropriately determined to achieve the target reaction time, considering the content of the supported metal catalyst and the amount of terephthalic acid to be used for the reaction. By using each raw material, etc. in an amount within the ranges described above, the yield and selectivity of 1,4-cyclohexanedicarboxylic acid to be obtained can be enhanced.

Next, the inside of the reactor is heated to a predetermined temperature to advance the nucleus hydrogenation reaction. The reaction temperature upon this is preferably 40 to 150° C., and the reaction pressure is preferably 0.5 to 15 MPa in terms of the hydrogen partial pressure. Note that the reaction time may be any length as long as it is long enough for the nucleus hydrogenation reaction to progress sufficiently. By adjusting the reaction conditions to be within the ranges mentioned above, the yield and selectivity of 1,4-cyclohexanedicarboxylic acid to be obtained can be enhanced. In addition, hydrogen gas may be appropriately introduced into the reactor in order to maintain the reaction pressure within the range described above.

In a fixed bed, for example, a reactor is first filled with a catalyst. The reactor is not particularly limited as long as the reactor functions as a fixed bed in such a way that the liquid reaction solution passes over the catalyst to provide a gas-liquid-solid mass transfer state. Hydrogen gas is distributed in that reactor and heated, thereby reducing and activating the catalyst. For the catalyst, for example, a catalyst used for an ordinary nucleus hydrogenation reaction can be employed, and more particularly, one or two or more metal catalysts, preferably precious metal catalysts, such as Ru, Pd, Pt and Rh, can be used. The catalyst may be those in which the metal catalyst described above as an active component is supported on one or two or more supports that are ordinarily used, such as carbon, $Al_2O_3$, $SiO_2$, $SiO_2$—$Al_2O_3$, $TiO_2$ and $ZrO_2$. When a support is used, it is preferable that the amount of the metal catalyst, which is an active component, to be supported should be 0.1 to 10% by mass based on 100% by mass of the support.

In addition, the pressure in the system upon the activation of the catalyst may be an ordinary pressure or may be compressed. When compressed, the pressure in the system is preferably 0.1 to 8 MPa, and hydrogen gas may be appropriately introduced into the reaction tube in order to maintain such a pressure. Furthermore, the activation temperature is preferably 50 to 300° C. By making conditions upon the activation of the catalyst within the ranges described above, the catalyst can be activated further more effectively and reliably. In addition, the heating time may be any length as long as it is sufficient for activating the catalyst.

Next, the reactor is cooled or heated as appropriate to achieve the reaction temperature, and hydrogen gas is introduced until reaching a predetermined pressure. The hydrogen gas is then introduced into the reactor at a predetermined flow rate. The pressure in the reactor may be an ordinary pressure or may be compressed. When compressed, the pressure in the system is preferably 0.5 to 15 MPa, and the reaction temperature is preferably 40 to 150° C. The flow rate of hydrogen is preferably an amount such that hydrogen is 300 to 1000 mol %, and more preferably an amount such that hydrogen is 300 to 600 mol % based on 100 mol % of terephthalic acid that comes into contact with the catalyst per unit time.

Next, an aqueous ammonia solution of terephthalic acid is formulated and distributed in the reactor using a pump. It is preferable that the concentration of terephthalic acid in the aqueous ammonia solution should be 2 to 20% by mass. In addition, it is preferable that the amount of the aqueous ammonia solution to be placed should be an amount that provides 200 to 400 mol % of ammonia based on 100 mol % of terephthalic acid. There is no limitation on the amount of the catalyst to be used, and it may be appropriately determined to achieve the target conversion rate, considering the content of the supported metal catalyst and amount of terephthalic acid to be used for the reaction. In addition, the reaction time may be any length as long as it is long enough for the nucleus hydrogenation reaction to progress sufficiently. By adjusting each reaction condition to be within the ranges described above, there is a tendency that the yield and selectivity of 1,4-cyclohexanedicarboxylic acid to be obtained can be enhanced.

When 1,4-cyclohexanedicarboxylic acid is produced in a manner as mentioned above, the obtained reaction solution includes an aqueous ammonia solution and the produced 1,4-cyclohexanedicarboxylic acid.

A production method for 1,4-dicyanocyclohexane of the present embodiment has a step (hereinafter, also simply referred to as a "cyanation step") of obtaining 1,4-dicyanocyclohexane by bringing a 1,4-cyclohexanedicarboxylic acid derivative obtained via the production method for a 1,4-cyclohexanedicarboxylic acid derivative of the present embodiment into contact with ammonia for a cyanation reaction. By using the 1,4-cyclohexanedicarboxylic acid derivative for the cyanation step, the yield of 1,4-dicyanocyclohexane can be increased compared to the case where, for example, cyanation is performed only by introducing ammonia gas into the system. The main cause is believed to be, without being limited to, that the heating at the heat concentration and precipitation step described above produces an intermediate in the 1,4-cyclohexanedicarboxylic acid derivative and this intermediate contributes to the cyanation reaction.

In the cyanation step, the 1,4-cyclohexanedicarboxylic acid derivative, a solvent as necessary, water as necessary, and a catalyst are placed in a reactor at first; and an inert gas is introduced until the pressure in the system reaches a predetermined pressure. Then, the inside of the reactor is heated to a predetermined temperature, and the inert gas is appropriately introduced into the reactor in order to maintain the pressure in the reactor within a constant range while stirring the inside of the reactor, thereby advancing the cyanation reaction.

In the cyanation step, no solvent may be used or a solvent may be used. It is preferable to use a solvent with a boiling point of 600° C. or less, more preferable to use a solvent with a boiling point of 500° C. or less, and still more preferable to use a solvent with a boiling point of 420° C. or less. Also, the solvent has a boiling point, which is equal to or higher than the reaction temperature of the cyanation reaction, of preferably 250° C. or more, more preferably 270° C. or more, and still more preferably 300° C. or more. When the boiling point is 300° C. or higher, the cyanation reaction progresses smoothly, and production of impurities such as a trimer of dicyanocyclohexane can often be suppressed. Specific examples of the solvent to be used in the cyanation step include: an aliphatic alkane such as heptadecane, nonadecane and docosane; an aliphatic alkene such as heptadecene, nonadecene and docosene; aliphatic alkyne such as heptadecyne, nonadecyne and docosyne; an alkyl-substituted aromatic such as alkylbenzene including undecylbenzene, tridecylbenzene and tetradecylbenzene, dialkylbenzene and alkylnaphthalene; an acid or acid anhydride such as 2,5-dichlorobenzoic acid and tetrachlorophthalic anhydride; an amide compound such as undecaneamide, lauric acid amide and stearic acid amide; a nitrile compound such as tetradecanenitrile, hexadecanenitrile, 2-naphthylacetonitrile, stearonitrile and 1,4-dicyanocyclohexane; a phosphorus compound such as p-chlorodiphenylphosphine and triphenyl phosphite; an amine such as 1,2-diphenylethylamine and trioctylamine; a hydroxide such as 2,2'-biphenol and triphenylmethanol; an ester such as benzyl benzoate and dioctyl phthalate; an ether such as 4-dibromophenyl ether; a halogenated benzene such as 1,2,4,5-tetrachloro-3-nitrobenzene and 4,4'-dichlorobenzophenone; a ketone such as 2-phenylacetophenone and anthraquinone; and triphenylmethane. Among these, as the solvent, one or more selected from the group consisting of alkylnaphthalene, triphenylmethane and dicyanocyclohexane are preferable from the viewpoint of being not likely to hinder progress of the cyanation reaction.

As the catalyst, a catalyst used for an ordinary cyanation reaction can be employed, and more particularly, examples of the catalyst include a metal oxide, such as silica gel, alumina, silica alumina, hydrotalcite, magnesium oxide, zinc oxide, tin oxide, iron oxide, titanium oxide, zirconium oxide, hafnium oxide, manganese oxide, tungsten oxide, vanadium pentoxide, niobium pentoxide, tantalum oxide, gallium oxide, indium oxide and scandium oxide. These may be a simple substance, a complex oxide, or those supported on a support. Examples of the supported component include, for example, an alkali metal such as sodium, lithium, potassium, rubidium and cesium, tin, rhenium, manganese, molybdenum, tungsten, vanadium, iron, nickel, zinc, chromium, boric acid, hydrochloric acid and phosphoric acid.

The catalyst to be used may be those in which the metal catalyst described above as an active component is supported on one or two or more supports that are ordinarily used, such as carbon, hydrotalcite, MgO, $Al_2O_3$, $SiO_2$, $SiO_2$—$Al_2O_3$, $TiO_2$ and $ZrO_2$. When a support is used, it is preferable that the amount of the metal catalyst, which is an active component, to be supported should be 0.1 to 10% by mass based on 100% by mass of the support.

In addition, examples of the catalyst also include a rhenium compound such as perrhenic acid and rhenium oxide, an organic tin compound such as dibutyltin oxide, a ruthenium compound such as dichlorotris(triphenylphosphine)ruthenium (II), and cobalt oxide.

Among these, as the catalyst, a catalyst including zinc oxide, tin oxide or iron oxide is preferable from the viewpoint of advancing the cyanation reaction more effectively and reliably. These catalysts are used alone as one kind or in combination of two or more kinds. Furthermore, it is preferable that the amount of the catalyst to be used should be 0.05 to 20% by mass based on 100% by mass of the 1,4-cyclohexanedicarboxylic acid derivative. By setting the amount of the catalyst within the range described above, there is a tendency that the yield of 1,4-dicyanocyclohexane to be obtained can be enhanced.

In addition, ammonia gas may be introduced into the reactor appropriately. Its flow rate may be appropriately adjusted according to the scale of reaction and the like, and normally, it is 0.1 to 5 moles per hour, preferably 0.3 to 4 moles per hour, and more preferably 0.5 to 3 moles per hour based on 1 mole of the 1,4-cyclohexanedicarboxylic acid derivative. It is preferable that the amount of the ammonia gas to be used should be 200 to 1000 mol % based on 100 mol % of the 1,4-cyclohexanedicarboxylic acid derivative. By doing this, there is a tendency that the yield and selectivity of 1,4-dicyanocyclohexane to be obtained can be enhanced.

The reaction temperature in the production method of the present embodiment is not particularly limited as long as it is a temperature at which the cyanation reaction progresses, and it is preferably 270 to 400° C., more preferably 280° C. to 380° C., and still more preferably 290° C. to 350° C.

The reaction pressure in the production method of the present embodiment may be a negative pressure, an ordinary pressure or a positive pressure.

The reaction time may be any length as long as it is long enough for the cyanation reaction to progress sufficiently. By adjusting the concentration of each raw material and the reaction conditions to be within the ranges mentioned above, there is a tendency that the yield of 1,4-dicyanocyclohexane can be enhanced.

1,4-Dicyanocyclohexane may be collected by distilling the reaction solution including 1,4-dicyanocyclohexane thus obtained, as necessary (hereinafter, this step is referred to as a "distillation step"). The distillation is performed by, for example, heating a distillation apparatus from the bottom section such that the pressure in the system in the distillation apparatus is 3.0 kPa to 4.0 kPa and the temperature is 180 to 230° C., and by cooling the top section, thereby performing gas-liquid contact in the apparatus. By doing this, 1,4-dicyanocyclohexane can be selectively drawn and collected from the top section of the distillation apparatus.

A production method for 1,4-bis(aminomethyl)cyclohexane of the present embodiment has a step (hereinafter, also simply referred to as a "nitrile hydrogenation step") of obtaining 1,4-bis(aminomethyl)cyclohexane by bringing 1,4-dicyanocyclohexane obtained as mentioned above into contact with hydrogen for a hydrogenation reaction (hereinafter, also referred to as a "nitrile hydrogenation reaction").

In the nitrile hydrogenation step, 1,4-dicyanocyclohexane, a solvent, and a catalyst are placed in a reactor at first; and hydrogen gas is introduced until the pressure in the system reaches a predetermined pressure. Then, the inside of the reactor is heated to a predetermined temperature, and hydrogen gas is appropriately introduced into the reactor in order to maintain the pressure in the reactor within a constant range, thereby advancing the nitrile hydrogenation reaction.

For the solvent, a solvent used for an ordinary nitrile hydrogenation reaction can be employed, and more particularly, examples of the solvent include an alcohol, such as methanol, ethanol, 1-propanol, 2-propanol, 1-butanol, 2-butanol and tert-butanol; an aromatic hydrocarbon, such as meta-xylene, mesitylene and pseudocumene; liquid ammonia; and aqueous ammonia. These solvents are used alone as one kind or in combination of two or more kinds. In addition, for the catalyst, for example, a catalyst used for an ordinary nitrile hydrogenation reaction can be employed, and more particularly, a catalyst containing Ni and/or Co can be used. Generally, for the catalyst, a catalyst made by supporting Ni and/or Co onto $Al_2O_3$, $SiO_2$, diatomaceous earth, $SiO_2$—$Al_2O_3$ or $ZrO_2$ by a precipitation method, Raney nickel, or Raney cobalt is suitably used. Among these, the Raney cobalt catalyst and Raney nickel catalyst are preferable from the viewpoint of advancing the nitrile hydrogenation reaction more effectively and reliably. These catalysts are used alone as one kind or in combination of two or more kinds. Furthermore, the amount of the catalyst to be used is preferably 0.1 to 150% by mass, more preferably 0.1 to 20% by mass, and still more preferably 0.5 to 15% by mass based on 100% by mass of 1,4-dicyanocyclohexane. By using the catalyst in an amount within the range described above, there is a tendency that the yield and selectivity of 1,4-bis(aminomethyl)cyclohexane to be obtained can be enhanced.

The concentration of 1,4-dicyanocyclohexane in the nitrile hydrogenation step is preferably 1 to 50% by mass and more preferably 2 to 40% by mass based on the entire amount of the reaction solution from the viewpoint of reaction efficiency. In addition, the reaction temperature in the nitrile hydrogenation step is preferably 40 to 150° C., and the reaction pressure is preferably 0.5 to 15 MPa in terms of the hydrogen partial pressure. Note that the reaction time may be any length as long as it is long enough for the nitrile hydrogenation reaction to progress sufficiently. By adjusting the reaction conditions to be within the ranges mentioned above, there is a tendency that the yield and selectivity of 1,4-bis(aminomethyl)cyclohexane to be obtained can be enhanced.

EXAMPLES

Hereinafter, the present invention will be further described in detail with reference to Examples, but the present invention is not limited to these Examples.

Nucleus Hydrogenation Step

Synthetic Example 1-1

A reaction tube made of SUS316 with an inner diameter of 17 mmφ and a length of 320 mm was filled with 12.63 g of 2% Ru/C (manufactured by N.E. CHEMCAT CORPORATION), which was a catalyst that had undergone gas phase hydrogen reduction at 250° C. for 2 hours in advance. The nucleus hydrogenation reaction was performed in an aqueous ammonia solution of 8% by mass terephthalic acid (ammonia/terephthalic acid=2.3 molar ratio) under the conditions of 15 to 27 g/hour, pressure: 3 to 9 MPaG, and hydrogen: 0.9 to 1.1 L/hour. At the stage 60 hours after the start of the reaction (90° C., 7 MPaG, flow rate of raw material: 15.4 g/hour, hydrogen: 0.9 L/hour), the conversion rate of terephthalic acid was 100% and the yield of 1,4-cyclohexanedicarboxylic acid was 99.9%. At the stage 1351 hours after the start of the reaction (75° C., 5 MPaG, flow rate of raw material: 26.6 g/hour, hydrogen: 1.1 L/hour), the conversion rate of terephthalic acid was 100% and the yield of 1,4-cyclohexanedicarboxylic acid was 99.9%. During the reaction, the content of trans isomer of 1,4-cyclohexanedicarboxylic acid remained between 20 and 24%.

The reaction solution was analyzed by HPLC (product name "Prominence" manufactured by Shimadzu Corporation; column: model name "KC-811" from Shodex; conditions: eluent: 0.1 mass % aqueous phosphoric acid, flow rate 0.7 mL/min, column temperature 50° C., photodiode array detector).

Heat Concentration and Precipitation Step

Synthetic Example 2-1

In a 300 ml four neck flask (flask) equipped with a stirring blade, a thermocouple, a condenser and a receiver, 16.11 g of 1,4-cyclohexanedicarboxylic acid manufactured by Tokyo Kasei Kogyo Co., Ltd., 11.38 g of 28% ammonia water, and 172.90 g of water were placed. While stirring at 300 rpm, the inside of the flask was heated to 150° C. with an oil bath at an ordinary pressure. Distillation started when the temperature of the liquid in the flask reached 105° C., and at the stage where the amount of distillation reached 170.7 g, the heating was stopped and the reaction solution was cooled. After cooling, the reaction solution was filtered and the crystal was collected. After vacuum drying the obtained crystal, elemental analysis was carried out thereon, and it was shown that the content of ammonia in the ammonium salt of 1,4-cyclohexanedicarboxylic acid is 1.14 in a molar ratio based on the content of 1,4-cyclohexanedicarboxylic acid in the ammonium salt of 1,4-cyclohexanedicarboxylic acid. There was no change found in the content of trans isomer in the 1,4-cyclohexanedicarboxylic acid derivative before and after the heat concentration.

Synthetic Example 2-2

In a 300 ml four neck flask (flask) equipped with a stirring blade, a thermocouple, a condenser, a receiver and a pressure reducing apparatus, 16.11 g of 1,4-cyclohexanedicarboxylic acid, 11.38 g of 28% ammonia water, and 172.90 g of water were placed. While stirring at 300 rpm, the inside of the flask was heated to 90° C. with an oil bath at a reduced pressure (20 kPa). Distillation started when the temperature of the liquid in the flask reached 65° C., and at the stage where the amount of distillation reached 168.7 g, the heating was stopped and the reaction solution was cooled. After cooling, the reaction solution was filtered and the crystal was collected. After vacuum drying the obtained crystal, elemental analysis was carried out thereon, and it was shown that the content of ammonia in the ammonium salt of 1,4-cyclohexanedicarboxylic acid is 1.61 in a molar ratio based on the content of 1,4-cyclohexanedicarboxylic acid in the ammonium salt of 1,4-cyclohexanedicarboxylic acid. There was no change found in the content of trans isomer in the 1,4-cyclohexanedicarboxylic acid derivative before and after the heat concentration.

Synthetic Example 2-3

In a 300 ml four neck flask (flask) equipped with a stirring blade, a thermocouple, a condenser, a receiver and a pressure reducing apparatus, 16.11 g of 1,4-cyclohexanedicarboxylic acid, 11.38 g of 28% ammonia water, and 172.90 g of water were placed. While stirring at 300 rpm, the inside of the flask was heated to 70° C. with an oil bath at a reduced pressure (4.5 kPa). Distillation started when the temperature of the liquid reached 35° C., and at the stage where the amount of distillation reached 159.2 g, the heating was stopped and the reaction solution was cooled. After cooling, the reaction solution was filtered and the crystal was collected. After vacuum drying the obtained crystal, elemental analysis was carried out thereon, and it was shown that the content of ammonia in the ammonium salt of 1,4-cyclohexanedicarboxylic acid is 1.81 in a molar ratio based on the content of 1,4-cyclohexanedicarboxylic acid in the ammonium salt of 1,4-cyclohexanedicarboxylic acid. There was no change found in the content of trans isomer in the 1,4-cyclohexanedicarboxylic acid derivative before and after the heat concentration.

Synthetic Example 2-4

In a 300 ml pressure resistant vessel made of SUS316 equipped with a stirring blade, a thermocouple, a pressure gauge, a condenser and a receiver, 16.12 g of 1,4-cyclohexanedicarboxylic acid, 12.55 g of 28% ammonia water, and 171.94 g of water were placed. While stirring at 600 rpm, the temperature was elevated until the internal temperature reached 140° C. After reaching 140° C., the purge valve was slightly opened and the gas component was condensed with the condenser to acquire the fraction. The internal pressure after reaching 140° C. was 0.41 MPaG, and the internal pressure during the distillation was 0.26 MPaG. At the stage where the amount of distillation reached 137.05 g, the heating was stopped and the reaction solution was cooled. After cooling, the reaction solution was filtered and the crystal was collected. The obtained 1,4-cyclohexanedicarboxylic acid derivative was 0.89 g, and the content of trans isomer was 91.8%.

Synthetic Example 2-5

In a 300 ml pressure resistant vessel made of SUS316 equipped with a stirring blade, a thermocouple, a pressure gauge, a condenser and a receiver, 16.12 g of 1,4-cyclohexanedicarboxylic acid, 12.55 g of 28% ammonia water, and 171.94 g of water were placed. While stirring at 600 rpm, the temperature was elevated until the internal temperature reached 160° C. After reaching 160° C., the purge valve was slightly opened and the gas component was condensed with the condenser to acquire the fraction. The internal pressure after reaching 160° C. was 0.57 MPaG, and the internal pressure during the distillation was 0.47 MPaG. At the stage where the amount of distillation reached 131.21 g, the heating was stopped and the reaction solution was cooled. After cooling, the reaction solution was filtered and the crystal was collected. The obtained 1,4-cyclohexanedicarboxylic acid derivative was 1.55 g, and the content of trans isomer was 90.9%.

Synthetic Example 2-6

In a 300 ml pressure resistant vessel made of SUS316 equipped with a stirring blade, a thermocouple, a pressure gauge, a condenser and a receiver, 16.12 g of 1,4-cyclohexanedicarboxylic acid, 12.55 g of 28% ammonia water, and 171.94 g of water were placed. While stirring at 600 rpm, the temperature was elevated until the internal temperature reached 200° C. After reaching 200° C., the purge valve was slightly opened and the gas component was condensed with the condenser to acquire the fraction. The internal pressure after reaching 200° C. was 1.38 MPaG, and the internal pressure during the distillation was 1.32 MPaG. At the stage where the amount of distillation reached 136.39 g, the heating was stopped and the reaction solution was cooled. After cooling, the reaction solution was filtered and the crystal was collected. The obtained 1,4-cyclohexanedicarboxylic acid derivative was 7.82 g, and the content of trans isomer was 98.4%.

Synthetic Example 2-7

First Heat Concentration

In a 300 ml pressure resistant vessel made of SUS316 equipped with a stirring blade, a thermocouple, a pressure gauge, a condenser and a receiver, 155.58 g of the reaction solution produced in Synthetic Example 1-1 (reaction solution extracted periodically between 541 and 962 hours after the start of the reaction) was placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.91 MPaG, and the internal pressure during the distillation was 0.71 MPaG. At the stage where the amount of distillation reached 105.23 g, the heating was stopped and the reaction solution was cooled to 45° C. After the internal temperature reached 45° C., the reaction solution was filtered and the crystal and the mother liquor were collected. The weight of the obtained crystal after vacuum drying was 3.04 g, and the content of ammonia in the ammonium salt of 1,4-cyclohexanedicarboxylic acid was 0.06 in a molar ratio based on the content of 1,4-cyclohexanedicarboxylic acid in the ammonium salt of 1,4-cyclohexanedicarboxylic acid. The content of trans isomer in the 1,4-cyclohexanedicarboxylic acid derivative was 96.40%. The weight of the obtained mother liquor was 40.92 g, almost all of which was used for the second heat concentration.

Second Heat Concentration

In a 300 ml pressure resistant vessel made of SUS316 equipped with a stirring blade, a thermocouple, a pressure gauge, a condenser and a receiver, 155.58 g of the reaction solution produced in Synthetic Example 1-1, which will be mentioned later, (reaction solution extracted periodically between 541 and 962 hours after the start of the reaction) and 40.82 g of the mother liquor after the first heat concentration were placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.87 MPaG, and the internal pressure during the distillation was 0.75 MPaG. At the stage where the amount of distillation reached 138.16 g, the heating was stopped and the reaction solution was cooled to 45° C. After the internal temperature reached 45° C., the reaction solution was filtered and the crystal and the mother liquor were collected. The weight of the obtained crystal after vacuum drying was 7.04 g, and the content of ammonia in the ammonium salt of 1,4-cyclohexanedicarboxylic acid was 0.14 in a molar ratio based on the content of 1,4-cyclohexanedicarboxylic acid in the ammonium salt of 1,4-cyclohexanedicarboxylic acid, and the content of trans isomer in the 1,4-cyclohexanedicarboxylic acid derivative was 94.87%. The weight of the obtained mother liquor was 47.76 g, almost all of which was used for the third heat concentration.

Third Heat Concentration

In a pressure resistant vessel, 155.61 g of the reaction solution produced in Synthetic Example 1-1 (reaction solution extracted periodically between 541 and 962 hours after the start of the reaction) and 47.42 g of the mother liquor after the second heat concentration were placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.86 MPaG, and the internal pressure during the distillation was 0.70 MPaG. At the stage where the amount of distillation reached 141.06 g, the heating was stopped and the reaction solution was cooled to 45° C. After the internal temperature reached 45° C., the reaction solution was filtered and the crystal and the mother liquor were collected. The weight of the obtained crystal after vacuum drying was 10.23 g, and the content of ammonia in the ammonium salt of 1,4-cyclohexanedicarboxylic acid was 0.33 in a molar ratio based on the content of 1,4-cyclohexanedicarboxylic acid in the ammonium salt of 1,4-cyclohexanedicarboxylic acid, and the content of trans isomer in the 1,4-cyclohexanedicarboxylic acid derivative was 89.17%. The weight of the obtained mother liquor was 47.03 g, almost all of which was used for the fourth heat concentration.

Fourth Heat Concentration

In a pressure resistant vessel, 155.62 g of the reaction solution produced in Synthetic Example 1-1 (reaction solution extracted periodically between 541 and 962 hours after the start of the reaction) and 46.78 g of the mother liquor after the third heat concentration were placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.85 MPaG, and the internal pressure during the distillation was 0.70 MPaG. At the stage where the amount of distillation reached 138.87 g, the heating was stopped and the reaction solution was cooled to 45° C. After the internal temperature reached 45° C., the reaction solution was filtered and the crystal and the mother liquor were collected. The weight of the obtained crystal after vacuum drying was 8.78 g, and the content of ammonia in the ammonium salt of 1,4-cyclohexanedicarboxylic acid was 0.30 in a molar ratio based on the content of 1,4-cyclohexanedicarboxylic acid in the ammonium salt of 1,4-cyclohexanedicarboxylic acid, and the content of trans isomer in the 1,4-cyclohexanedicarboxylic acid derivative was 89.22%. The weight of the obtained mother liquor was 46.36 g, almost all of which was used for the fifth heat concentration.

Fifth Heat Concentration

In a pressure resistant vessel, 155.88 g of the reaction solution produced in Synthetic Example 1-1 (reaction solution extracted periodically between 541 and 962 hours after the start of the reaction) and 47.21 g of the mother liquor after the fourth heat concentration were placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.85 MPaG, and the internal pressure during the distillation was 0.69 MPaG. At the stage where the amount of distillation reached 139.62 g, the heating was stopped and the reaction solution was cooled to 45° C. After the internal temperature reached 45° C., the reaction solution was filtered and the crystal and the mother liquor were collected. The weight of the obtained crystal after vacuum drying was 14.75 g, and the content of ammonia in the ammonium salt of 1,4-cyclohexanedicarboxylic acid was 0.43 in a molar ratio based on the content of 1,4-cyclohexanedicarboxylic acid in the ammonium salt of 1,4-cyclohexanedicarboxylic acid, and the content of trans isomer in the 1,4-cyclohexanedicarboxylic acid derivative was 83.14%. The weight of the obtained mother liquor was 43.96 g, almost all of which was used for the sixth heat concentration.

Sixth Heat Concentration

In a pressure resistant vessel, 155.61 g of the reaction solution produced in Synthetic Example 1-1 (reaction solution extracted periodically between 541 and 962 hours after the start of the reaction) and 44.08 g of the mother liquor after the fifth heat concentration were placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.85 MPaG, and the internal pressure during the distillation was 0.65 MPaG. At the stage where the amount of distillation reached 141.61 g, the heating was stopped and the reaction solution was cooled to 45° C. After the internal temperature reached 45° C., the reaction solution was filtered and the crystal and the mother liquor were collected. The weight of the obtained crystal after vacuum drying was 12.82 g, and the content of ammonia in the ammonium salt of 1,4-cyclohexanedicarboxylic acid was 0.39 in a molar ratio based on the content of 1,4-cyclohexanedicarboxylic acid in the ammonium salt of 1,4-cyclohexanedicarboxylic acid, and the content of trans isomer in the 1,4-cyclohexanedicarboxylic acid derivative was 80.85%. The weight of the obtained mother liquor was 37.45 g, almost all of which was used for the seventh heat concentration.

Seventh Heat Concentration

In a pressure resistant vessel, 155.58 g of the reaction solution produced in Synthetic Example 1-1 (reaction solution extracted periodically between 541 and 962 hours after the start of the reaction) and 33.33 g of the mother liquor after the sixth heat concentration were placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.85 MPaG, and the internal pressure during the distillation was 0.65 MPaG. At the stage where the amount of distillation reached 125.4 g, the heating was stopped and the reaction solution was cooled to 45° C. After the internal temperature reached 45° C., the reaction solution was filtered and the crystal and the mother liquor were collected. The weight of the obtained crystal after vacuum drying was 9.81 g, and the content of ammonia in the ammonium salt of 1,4-cyclohexanedicarboxylic acid was 0.31 in a molar ratio based on the content of 1,4-cyclohexanedicarboxylic acid in the ammonium salt of 1,4-cyclohexanedicarboxylic acid, and the content of trans isomer in the 1,4-cyclohexanedicarboxylic acid derivative was 87.00%. The weight of the obtained mother liquor was 50.33 g, almost all of which was used for the eighth heat concentration.

Eighth Heat Concentration

In a pressure resistant vessel, 155.62 g of the reaction solution produced in Synthetic Example 1-1 (reaction solution extracted periodically between 541 and 962 hours after the start of the reaction) and 49.92 g of the mother liquor after the seventh heat concentration were placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.85 MPaG, and the internal pressure during the distillation was 0.65 MPaG. At the stage where the amount of distillation reached 138.7 g, the heating was stopped and the reaction solution was cooled to 45° C. After the internal temperature reached 45° C., the reaction solution was filtered and the crystal and the mother liquor were collected. The weight of the obtained crystal after vacuum drying was 10.29 g, and the content of ammonia in the ammonium salt of 1,4-cyclohexanedicarboxylic acid was 0.31 in a molar ratio based on the content of 1,4-cyclohexanedicarboxylic acid in the ammonium salt of 1,4-cyclohexanedicarboxylic acid, and the content of trans isomer in the 1,4-cyclohexanedicarboxylic acid derivative was 90.72%. The weight of the obtained mother liquor was 50.97 g, almost all of which was used for the ninth heat concentration.

Ninth Heat Concentration

In a pressure resistant vessel, 155.67 g of the reaction solution produced in Synthetic Example 1-1 (reaction solution extracted periodically between 541 and 962 hours after the start of the reaction) and 51.21 g of the mother liquor after the eighth heat concentration were placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.85 MPaG, and the internal pressure during the distillation was 0.65 MPaG. At the stage where the amount of distillation reached 140.78 g, the heating was stopped and the reaction solution was cooled to 45° C. After the internal temperature reached 45° C., the reaction solution was filtered and the crystal and the mother liquor were collected. The weight of the obtained crystal after vacuum drying was 15.80 g, and the content of ammonia in the ammonium salt of 1,4-cyclohexanedicarboxylic acid was 0.45 in a molar ratio based on the content of 1,4-cyclohexanedicarboxylic acid in the ammonium salt of 1,4-cyclohexanedicarboxylic acid, and the content of trans isomer in the 1,4-cyclohexanedicarboxylic acid derivative was 82.24%. The weight of the obtained mother liquor was 45.23 g, almost all of which was used for the tenth heat concentration.

Tenth Heat Concentration

In a pressure resistant vessel, 155.68 g of the reaction solution produced in Synthetic Example 1-1 (reaction solution extracted periodically between 541 and 962 hours after the start of the reaction) and 45.17 g of the mother liquor after the ninth heat concentration were placed. While stirring at 600 rpm, the temperature was elevated until the internal temperature reached 180° C. After reaching 180° C., the purge valve was slightly opened and the gas component was condensed with the condenser to acquire the fraction. The internal pressure after reaching 180° C. was 0.85 MPaG, and the internal pressure during the distillation was 0.65 MPaG. At the stage where the amount of distillation reached 135.78 g, the heating was stopped and the reaction solution was cooled to 45° C. After the internal temperature reached 45° C., the reaction solution was filtered and the crystal and the mother liquor were collected. The weight of the obtained crystal after vacuum drying was 10.89 g, and the content of ammonia in the ammonium salt of 1,4cyclohexanedicarboxylic acid was 0.27 in a molar ratio based on the content of 1,4-cyclohexanedicarboxylic acid in the ammonium salt of 1,4-cyclohexanedicarboxylic acid, and the content of trans isomer in the 1,4-cyclohexanedicarboxylic acid derivative was 89.79%. The weight of the obtained mother liquor was 49.05 g.

Cyanation Step

Synthetic Example 3-1

In a 300 mL five neck flask equipped with a stirring blade, a gas introduction tube, a thermocouple and a dehydration apparatus, 51.6 g of an ammonium salt of 1,4-cyclohexanedicarboxylic acid produced according to the method described in Synthetic Example 2-7 (the content of ammonia in the ammonium salt of 1,4-cyclohexanedicarboxylic acid was 0.34 in a molar ratio based on the content of 1,4-cyclohexanedicarboxylic acid in the ammonium salt of 1,4-cyclohexanedicarboxylic acid), 0.20 g of zinc oxide (manufactured by Kanto Chemical Co., Inc.) as a catalyst, and 50 g of 1,4-dicyanocyclohexane were placed. Then, heating was started, and nitrogen gas (flow rate: 34 NmL/min) and ammonia gas (flow rate: 174 NmL/min) were introduced at 170° C. After further elevating the temperature, bubbling in the reaction solution was started at 270° C., and the temperature was elevated to 300° C. The reaction solution was stirred at 300 rpm for 7 hours to carry out a cyanation reaction. After the reaction finished, the reaction product was dissolved in tetrahydrofuran, and after further removing the catalyst in the solution by filtration, the reaction product was analyzed by gas chromatography (hereinafter, also described as GC) (model name "GC2010 PLUS" manufactured by Shimadzu Corporation, column: product name "HP-5ms" manufactured by Agilent Technologies, 30 m length×0.25 mm i.d., film thickness 0.25 µm). As a result, the yield of 1,4-dicyanocyclohexane was 90.8 mol %.

Synthetic Example 3-2

In a 100 mL five neck flask equipped with a stirring blade, a gas introduction tube, a thermocouple and a dehydration apparatus, 51.6 g of an ammonium salt of 1,4-cyclohexanedicarboxylic acid produced according to the method described in Example 2-7 (the content of ammonia in the ammonium salt of 1,4-cyclohexanedicarboxylic acid was 0.34 in a molar ratio based on the content of 1,4-cyclohexanedicarboxylic acid in the ammonium salt of 1,4-cyclohexanedicarboxylic acid) and 0.20 g of zinc oxide (manufactured by Kanto Chemical Co., Inc.) as a catalyst were placed. Then, heating was started, and nitrogen gas (flow rate: 34 NmL/min) and ammonia gas (flow rate: 174 NmL/min) were introduced at 170° C. After further elevating the temperature, bubbling in the reaction solution was started at 270° C., and the temperature was elevated to 300° C. The reaction solution was stirred at 300 rpm for 7 hours to carry out a cyanation reaction. After the reaction finished, the same operation as in Synthetic Example 3-1 was carried out, and analysis by GC was carried out. The yield of 1,4-dicyanocyclohexane was 92.8 mol %.

Synthetic Example 3-3

In a 500 mL five neck flask equipped with a stirring blade, a gas introduction tube, a thermocouple and a dehydration apparatus, 103.2 g of an ammonium salt of 1,4-cyclohexanedicarboxylic acid produced according to the method described in Example 2-7 (the content of ammonia in the ammonium salt of 1,4-cyclohexanedicarboxylic acid was 0.34 in a molar ratio based on the content of 1,4-cyclohexanedicarboxylic acid in the ammonium salt of 1,4-cyclohexanedicarboxylic acid), 0.40 g of zinc oxide (manufactured by Kanto Chemical Co., Inc.) as a catalyst, and 200 g of BARREL process oil B-28AN (manufactured by MATSUMURA OIL Co., Ltd.) were placed. Then, heating was started, and nitrogen gas (flow rate: 34 NmL/min) and ammonia gas (flow rate: 174 NmL/min) were introduced at 170° C. After further elevating the temperature, bubbling in the reaction solution was started at 270° C., and the temperature was elevated to 300° C. The reaction solution was stirred at 300 rpm for 8 hours to carry out a cyanation reaction. After the reaction finished, the same operation as in Synthetic Example 3-1 was carried out, and analysis by GC was carried out. The yield of 1,4-dicyanocyclohexane was 92.1 mol %.

Nitrile Hydrogenation Step

Synthetic Example 4-1

In a 300 mL pressure resistant vessel made of SUS316, 24.4 g of 1,4-dicyanocyclohexane, 37.3 g of methanol and 28.4 g of 28% ammonia water (manufactured by Wako Pure Chemical Industry Co., Ltd.) as solvents, and 0.56 g of Raney cobalt catalyst (manufactured by Wako Pure Chemical Industry Co., Ltd.) as a catalyst were placed, and hydrogen gas was introduced until reaching a reaction pressure of 4.5 MPa. Next, the inside of the vessel was heated to a reaction temperature of 80° C., and while retaining the constant temperature and stirring the inside of the vessel with an electromagnetic stirring blade at 750 rpm, an amination reaction by hydrogenation (nitrile hydrogenation reaction) was advanced for 240 minutes. After the reaction finished, the catalyst was removed by filtration, and the reaction product was then analyzed by gas chromatography (model name "GC2010 PLUS" manufactured by Shimadzu Corporation, column: product name "HP-5ms" manufactured by Agilent Technologies, 30 m length×0.25 mm i.d., film thickness 0.25 μm). As a result, the conversion rate of 1,4-dicyanocyclohexane was 100%, and the selectivity and the yield of 1,4-bis(aminomethyl)cyclohexane were 97.0% and 97.0%, respectively.

Synthetic Example 4-2

In a 300 mL pressure resistant vessel made of SUS316, 38.2 g of 1,4-dicyanocyclohexane, 111.6 g of liquid ammonia as a solvent, and 3.31 g of Raney cobalt catalyst (manufactured by Wako Pure Chemical Industry Co., Ltd.) as a catalyst were placed, and hydrogen gas was introduced until reaching a reaction pressure of 8.0 MPa. Next, the inside of the vessel was heated to a reaction temperature of 90° C., and while retaining the constant temperature and stirring the inside of the vessel with an electromagnetic stirring blade at 750 rpm, an amination reaction by hydrogenation (nitrile hydrogenation reaction) was advanced for 60 minutes. After the reaction finished, the same operation as in Synthetic Example 4-1 was carried out, and analysis by GC was carried out. As a result, the conversion rate of 1,4-dicyanocyclohexane was 100%, and the selectivity and the yield of 1,4-bis(aminomethyl)cyclohexane were 99.4% and 99.4%, respectively.

Comparative Example 1

In a 300 mL pressure resistant vessel made of SUS316, 25 g of terephthalic acid (manufactured by Tokyo Kasei Kogyo Co., Ltd.), 5.30 g (2.5 g on dried basis) of a 5% Ru/C catalyst (manufactured by N.E. CHEMCAT CORPORATION, type A, water content: 52.8% by mass) as a catalyst, 100 g of water, and 75 ml of a 5N NaOH aqueous solution (manufactured by Wako Pure Chemical Industries, Ltd.) were placed. Next, the inside of the vessel was heated to a reaction temperature of 100° C., and while retaining the constant temperature, introducing hydrogen gas until reaching a reaction pressure of 8 MPa, retaining the constant hydrogen pressure, and stirring the inside of the vessel with an electromagnetic stirring blade at 800 rpm, a nucleus hydrogenation reaction was advanced for 360 minutes. After the reaction finished, the catalyst in the reaction solution was removed by filtration. Then, 75 ml of a 5N HCl aqueous solution (manufactured by Wako Pure Chemical Industries, Ltd.) was dropped to the reaction solution, thereby precipitating a crystal. The precipitated crystal was collected by filtration, and the collected crystal was rinsed with pure water. The removal of NaCl from the crystal required two rinses with pure water. 1,4-Cyclohexanedicarboxylic acid is also dissolved in the mother liquor and the rinsing solution, leading to a decrease in yield due to loss. NaCl was produced in an amount corresponding to the amounts of NaOH and HCl placed.

The present application is based on Japanese Patent Application No. 2018-076270 filed in the Japan Patent Office on Apr. 11, 2018, the contents of which are incorporated herein by reference.

INDUSTRIAL APPLICABILITY

Since the 1,4-cyclohexanedicarboxylic acid derivative and 1,4-dicyanocyclohexane to be obtained according to the production methods of the present invention can be a raw material for bis(aminomethyl)cyclohexane, which is effective as an optical material for a plastic lens, prism, optical fiber, information recording substrate, filter, etc., used for polyamide, polyurethane and the like, it has an industrial applicability in such fields.

The invention claimed is:

1. A method for producing a 1,4-cyclohexanedicarboxylic acid derivative, the method comprising:
    heat concentrating an aqueous ammonia solution comprising 1,4-cyclohexanedicarboxylic acid, thereby precipitating a 1,4-cyclohexanedicarboxylic acid derivative as a crystal,
    wherein the 1,4-cyclohexanedicarboxylic acid derivative is an ammonium salt of 1,4-cyclohexanedicarboxylic acid and/or 4-carboxamidocyclohexane-1-carboxylic acid, and a content of trans isomer of the 1,4-cyclohexanedicarboxylic acid derivative is 70.0 to 99.9 wt. %.

2. The method of claim 1, wherein the 1,4-cyclohexanedicarboxylic acid derivative is an ammonium salt of 1,4-cyclohexanedicarboxylic acid and 4-carboxamidocyclohexane-1-carboxylic acid.

3. The method of claim 2, wherein the ammonium salt of 1,4-cyclohexanedicarboxylic acid is present and a molar ratio of ammonia to 1,4-cyclohexanedicarboxylic acid in the ammonium salt is in a range of from 0.01 to 2.00.

4. The method of claim 1, wherein the heat concentrating is conducted at a temperature in a range of from 30 to 200° C.

5. The method of claim 1, wherein, in the heat concentrating, the heat concentration is conducted at a pressure in a range of from 0.003 to 2 MPa.

6. The method of claim 1, wherein the aqueous ammonia solution is obtained by subjecting an aqueous ammonia solution comprising terephthalic acid to nucleus hydrogenation.

7. A method for producing 1,4-dicyanocyclohexane, the method comprising:
obtaining 1,4-dicyanocyclohexane by bringing a 1,4-cyclohexanedicarboxylic acid derivative obtained via the method of claim 1 into contact with ammonia for a cyanation reaction.

8. A method for producing 1,4-bis(aminomethyl)cyclohexane, the method comprising:
obtaining 1,4-bis(aminomethyl)cyclohexane by bringing 1,4-dicyanocyclohexane obtained via the method of claim 7 into contact with hydrogen for a hydrogenation reaction.

9. The method of claim 1, wherein the aqueous ammonia solution before the heat concentrating has an ammonia concentration in a range of from 0.1 to 10 wt. % based on total aqueous ammonia solution mass.

10. The method of claim 1, wherein the heat concentrating is conducted at a temperature in a range of from 50 to 200° C.

11. The method of claim 1, wherein the heat concentrating is conducted at a temperature in a range of from 100 to 200° C.

12. The method of claim 1, wherein the heat concentrating is conducted at a temperature in a range of from 120 to 200° C.

13. The method of claim 1, wherein the heat concentrating is conducted at a temperature in a range of from 140 to 200° C.

14. The method of claim 1, wherein a content of trans isomer of the 1,4-cyclohexanedicarboxylic acid derivative is 75.0 to 99.0 wt. %.

15. The method of claim 1, wherein a content of trans isomer of the 1,4-cyclohexanedicarboxylic acid derivative is 78.0 to 98.0 wt. %.

16. The method of claim 1, wherein a content of trans isomer of the 1,4-cyclohexanedicarboxylic acid derivative is 80.0 to 96.0 wt. %.

17. The method of claim 1, further comprising:
filtering off the crystal,
wherein a mother liquor after the filtering comprises 5 to 35 wt. %.

* * * * *